(12) United States Patent
Anthonavage et al.

(10) Patent No.: US 8,722,113 B2
(45) Date of Patent: May 13, 2014

(54) COMPOSITIONS COMPRISING EXTRACTS OF SOUTHERNWOOD AND AN AMINE COMPOUND

(75) Inventors: Michael Anthonavage, Lebanon, NJ (US); Meghan Russell, Lawrenceville, NJ (US); Samantha Tucker-Samaras, Long Valley, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 13/280,668

(22) Filed: Oct. 25, 2011

(65) Prior Publication Data

US 2012/0276226 A1 Nov. 1, 2012

Related U.S. Application Data

(60) Division of application No. 12/967,113, filed on Dec. 14, 2010, now abandoned, which is a continuation-in-part of application No. 12/775,938, filed on May 7, 2010, now abandoned.

(51) Int. Cl.
| | |
|---|---|
| A61K 36/282 | (2006.01) |
| A61K 8/41 | (2006.01) |
| A61K 8/97 | (2006.01) |
| A61K 31/132 | (2006.01) |
| A61K 31/133 | (2006.01) |

(52) U.S. Cl.
CPC .......... *A61K 36/282* (2013.01); *A61K 8/41* (2013.01); *A61K 8/97* (2013.01); *A61K 31/132* (2013.01); *A61K 31/133* (2013.01)
USPC ............................ 424/740; 424/401; 514/669

(58) Field of Classification Search
CPC . A61K 36/282; A61K 31/132; A61K 31/133; A61K 8/97; A61K 8/41; A61K 2300/00
USPC ................... 424/740, 401; 514/669
See application file for complete search history.

(56) References Cited

U.S. PATENT DOCUMENTS

| | | |
|---|---|---|
| 6,254,858 B1 | 7/2001 | Shim |
| 6,403,656 B1 | 6/2002 | Rivier et al. |
| 2006/0193814 A1 | 8/2006 | Ruvolo et al. |
| 2006/0193815 A1 | 8/2006 | Southall et al. |
| 2006/0193818 A1 | 8/2006 | Southall et al. |
| 2006/0257335 A1 | 11/2006 | Southall et al. |
| 2007/0042010 A1 | 2/2007 | Southall et al. |
| 2008/0260869 A1 | 10/2008 | Faller et al. |
| 2009/0227683 A1 | 9/2009 | Liebel et al. |
| 2009/0285868 A1 | 11/2009 | Richard et al. |
| 2010/0305064 A1 | 12/2010 | Walsh |

FOREIGN PATENT DOCUMENTS

| | | |
|---|---|---|
| EP | 1335740 B1 | 8/2003 |
| EP | 2 123 248 A1 | 11/2009 |
| FR | 2 773 075 A1 | 7/1999 |
| FR | 2835184 A1 | 8/2003 |
| FR | 2890312 A1 | 3/2007 |
| KR | 20100057157 A | 5/2010 |
| WO | WO 02/34229 A1 | 5/2002 |
| WO | WO 03/022294 A2 | 3/2003 |
| WO | WO 2007/004952 A1 | 1/2007 |

OTHER PUBLICATIONS

Database WPI Week 201082, Thomson Scientific, London, GB; AN 2010-H3707, XP000002657444, & KR 2010 0057157 A (The Faceshop Co Ltd) May 31, 2010 Abstract.

Rawlings et al., "Abnormalities in stratum corneum structure, lipid composition, and desomosome degradation in soap-induced winter xerosis", J. Soc. Cosmet. Chem. 45: 203-220, Jul./Aug. 1994.

Rawlings et al., "Effect of lactic acid isomers on keratinocyte ceramide synthesis, stratum corneum lipid levels and stratum corneum barrier function", Arch. Dermatol. Res. (1996) 288:383-390.

Russell, M. et al., "Clinical benefits of topical application of *Artemisia abrotanum* (Southernwood) on photo-damaged skin", Journal of Investigative Dermatology, Nature Publishing Group, GB, vol. 131, No. Suppl. 1, Apr. 1, 2011, p. S92, XP009151465, ISSN: 0022-202X, Abstract.

Russell, M. et al., "The effects of *Artemisia abrotanum* (Southernwood) on multiple levels of the skin", Journal of Investigative Dermatology, Nature Publishing Group, GB, vol. 131, No. Suppl. 1, Apr. 1, 2011, p. S60, XP009151464, ISSN: 0022-202X, Abstract.

Tanno et al., "Nicotinamide increases biosynthesis of ceramides as well as other stratum corneum lipids to improve the epidermal permeability barrier", British Journal of Dermatology 2000: 143:524-531.

PCT Intl. Search Report for PCT/US2011/035200 dated Sep. 1, 2011.

*Primary Examiner* — Susan Hoffman
(74) *Attorney, Agent, or Firm* — Sharon E. Hayner

(57) ABSTRACT

The present invention relates to compositions comprising a Southernwood extract and an amine compound, and methods treating skin with said compositions.

5 Claims, No Drawings

COMPOSITIONS COMPRISING EXTRACTS OF SOUTHERNWOOD AND AN AMINE COMPOUND

CROSS REFERENCE TO RELATED APPLICATIONS

This application is a division of U.S. application Ser. No. 12/967,113 filed Dec. 14, 2010, now abandoned which is a continuation-in-part of U.S. application Ser. No. 12/775,938 filed May 7, 2010, now abandoned the disclosures of which are hereby incorporated by reference in their entirety.

FIELD OF THE INVENTION

The present invention relates to compositions comprising extracts of Southernwood and an amine compound, as well as methods of using these compositions. The compositions are useful, for example for treating visibly dry skin.

BACKGROUND OF THE INVENTION

The top layer of human skin, the stratum corneum (SC) consists of protein enriched corneocytes embedded in a lipid matrix. The major function of the structure, as the body's protective barrier to the environment that prevents the loss of water and nutrients from within, is predominantly determined by the levels, composition and structure of the SC lipids. The SC lipids also influence the mechanical and desquamatory (skin cell shedding) activities of the SC. Abnormalities in the SC lipids can occur in connection with various conditions such as aged or photo damaged skin, or in connection with xerosis (a condition of abnormal dryness) such as during winter months.

Replenishing SC lipids by topical application of hydrophobic compounds is an approach that has been used with limited success. A longer lasting approach is to exploit the robust epidermal lipid biosynthetic pathways of the viable epidermis using natural extracts or compounds that upregulate the body's natural production of these lipids, and particularly a class of critically important SC lipids known as ceramides. Nicotinamide, for example, has been reported to increase the synthesis of ceramides, major constituents of lipids present as lamellar sheets in intercellular spaces of the SC. *Br. J. Dermatol.* (2000 September) 143(3):524-31. In addition, certain isomers of lactic acid are also reported to stimulate ceramide biosynthesis. *Arch. Dermatol. Res.* (1996) 288: 383-390.

It is well recognized that ceramides are functionally and structurally distinct from lipids that are present in deeper layers (i.e., the hypodermis) of the skin. For example, while ceramides are a class of polar lipids that play a role in cell membrane structures to enhance skin barrier function, the deeper hypodermal lipids are non-polar lipids whose function relates to energy storage, thermal insulation, and protection of internal organs from mechanical injury.

It has been reported that Southernwood extract is suitable for "fat restructuring" and stimulating adipogenesis, presumably by affecting the non-polar lipids of hypodermis. See US 2009/0285868 A1. Surprisingly, the inventors have now found that Southernwood extract, acting on an entirely different biological pathway, is suitable to enhance the biosynthesis of ceramides. Accordingly, the inventors have found that Southernwood extracts are remarkably suitable for treating completely different need states, and completely different skin, than what is known in the art. Specifically, the inventors have found that Southernwood extract is surprisingly suitable for the topical treatment of visibly dry, e.g., xerotic skin.

Furthermore, the inventors have now found that Southernwood extracts, when combined with particular amine compounds, provide surprisingly improved ability to enhance ceramide synthesis as well as maintain hydration (water levels) in the upper layers of the stratum corneum.

SUMMARY OF THE INVENTION

The present invention relates to a composition comprising a Southernwood extract and an amine compound of formula I or formula II shown below:

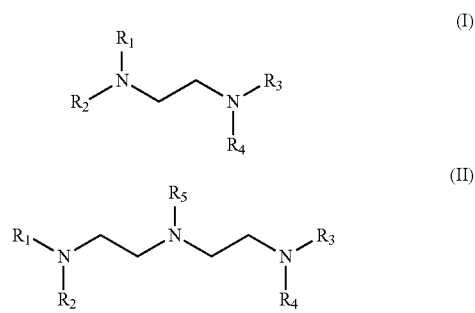

wherein $R_1$, $R_2$, $R_3$, $R_4$, and $R_5$ independently are selected from the group consisting of hydrogen, C1-C6 alkyl, and C1-C6 hydroxyalkyl; or a cosmetically-acceptable salt thereof.

The compositions may be used to treating visibly dry skin. Accordingly, in another aspect the invention relates to a method for treating visibly dry skin. The method includes topically applying to said skin, a composition comprising a Southernwood extract and an amine compound described above.

Other features and advantages of the present invention will be apparent from the detailed description of the invention and from the claims.

DETAILED DESCRIPTION OF PREFERRED EMBODIMENTS

Unless defined otherwise, all technical and scientific terms used herein have the same meaning as commonly understood by one of ordinary skill in the art to which the invention pertains. Also, all publications, patent applications, patents, and other references mentioned herein are incorporated by reference. Unless otherwise indicated, a percentage refers to a percentage by weight (i.e., % (W/W). Unless stated otherwise, all ranges are inclusive of the endpoints, e.g., "from 4 to 9" includes the endpoints 4 and 9.

As used herein, "visibly dry skin" refers to dry or dehydrated skin that shows visible signs of flaking. In certain embodiments of the invention, visibly dry skin is characterized clinically according to Rawlings et al., *J. Soc. Cosmet. Chem.* 45: 203-220 July/August 1994, in one or more of the following manners: skin having small flakes of dry skin and whitening of dermatoglyphic triangles (mild xerosis); skin having small, dry flakes giving a light powdery appearance—corners of dermatoglyphic triangles have started to uplift (moderate xerosis); or skin in which the entire length of a number of dermatoglyphic triangles have uplifted to generate large, dry skin flakes—roughness is very evident (well-defined xerosis). In certain other embodiments of the invention, the visibly dry skin has deficient levels of ceramides in the stratum corneum.

In certain embodiments, the visibly dry skin may be, but is not necessarily, classified as skin having compromised barrier properties, or skin characterized by certain disease states such as eczematic skin, psoriatic skin, or skin characterized by atopic dermatitis. As used herein, "eczema" refers to a chronic skin disorder that involves inflammation of the epidermis and often presents as scaly and itchy rashes. As used herein, "atopic dermatitis" refers to a type of chronically relapsing, non-contagious and pruritic form of eczema. As used herein, "psoriasis" refers to a chronic, non-infectious disease that presents as red, scaly patches or plaques of excessive inflammation or excessive skin production, often present on extensor surfaces such as knees and elbows.

The visibly dry skin may be present on the face or body, including the hands, feet, scalp, elbows, knees, ankles, nape of the neck, among other areas of the body.

As used herein, "treating" refers to mitigating, reducing, preventing, improving, or eliminating the presence or appearance of a condition or disease.

As used herein, "cosmetic" refers to a beautifying substance or preparation which preserves, restores, bestows, simulates, or enhances the appearance of bodily beauty or appears to enhance beauty or youthfulness, specifically as it relates to the appearance of tissue or skin.

As used herein, "cosmetically acceptable" means suitable for use in contact with (human) tissues (e.g., the skin) without undue toxicity, incompatibility, instability, irritation, allergic response, and the like, commensurate with a reasonable benefit/risk ratio.

It is believed that one skilled in the art can, based upon the description herein, utilize the present invention to its fullest extent. The following specific embodiments are to be construed as merely illustrative, and not limitative of the remainder of the disclosure in any way whatsoever.

Southernwood Extract

As used herein the term "Southernwood" refers to plants of the genus/species *Artemisia abrotanum*. As used herein the term "extract of Southernwood" or "Southernwood extract" refers to extract obtained from one or more parts of the Southernwood plant (e.g., flower, seed, root, rhizome, stem, fruit and/or leaf), which may be optionally isolated. The Southernwood extract may for example be prepared by finely dividing the harvested plant or parts thereof, such as by crushing, grinding, or milling to a finely divided solid or powder. The plant or portions thereof are preferably contacted with a solvent, e.g., steam, water (that may or not be heated), or other solvents, to extract portions thereof. In certain embodiments of the invention, the Southernwood extract comprises a mixture of oligosaccharides.

In certain embodiments, the Southernwood extract comprises oligosaccharides having a degree of polymerization of 1 to 4, and polyphenols. In another embodiment, the Southernwood extract comprises oligosaccharides having a degree of polymerization of 1 to 4, proteins, and polyphenols. For example, the Southernwood extract may have an actives content (i.e., the portion that excludes all solvents employed in the extraction process) comprising about 1% polyphenols, about 16% proteins, and about 83% saccharides having a degree of polymerization of 1 to 4. The saccharides may comprise monosaccharides, trisaccharides, and tetrasaccharides. In one embodiment, the saccharides may include monosaccharides (e.g., about 54%), trisaccharides (about 12%), and tetrasaccharides (e.g., about 34%).

The amount of Southernwood extract in the composition may be from about 0.5% to about 10% by weight of the composition, preferably from about 0.5% to about 5%, more preferably from about 0.75% to about 5%, even more preferably from about 1% to about 4%, and most preferably from about 2% to about 3%.

One particularly suitable Southernwood extract is commercially available as PULPACTYL from Silab of France, which is an aqueous-glycolic extract of Southernwood and includes water and butylene glycol.

A suitable extraction process may comprise contacting one or more parts of the Southernwood plant with a solvent system comprising water and/or butylene glycol.

For example, the plant may be powdered and mixed in a water/butylene glycol mixture, phase separated, filtered and sterilized. See, e.g., FR2890312 A1.

Amine Compound

Compositions of the present invention include an amine compound of formula I or formula II:

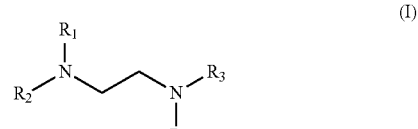

(I)

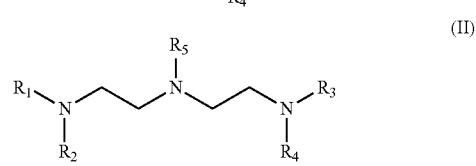

(II)

wherein $R_1$, $R_2$, $R_3$, $R_4$, and $R_5$ independently are selected from the group consisting of hydrogen, C1-C6 alkyl, and C1-C6 hydroxyalkyl; or a cosmetically-acceptable salt thereof.

Examples of preferred amine compounds of formula I include, but are not limited to, N,N,N',N'-Tetrakis(2-hydroxypropyl)ethylenediamine (THPED), N,N,N',N'-Tetrakis(2-hydroxyethyl)ethylene diamine (THEED), and N,N,N',N'-tetramethylethylene diamine (TEMED), the structures of which are set forth below, enantiomers thereof, diastereoisomers thereof, and cosmetically-acceptable salts thereof.

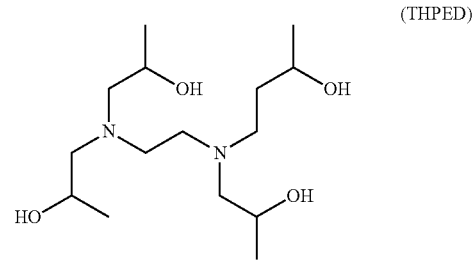

(THPED)

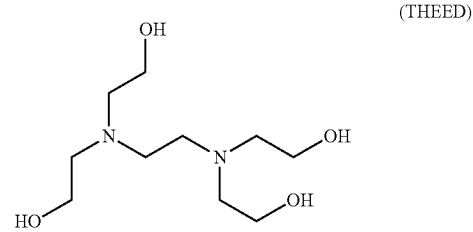

(THEED)

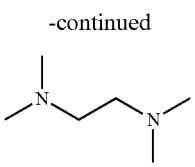
(TEMED)

In a preferred embodiment, the amine compound is THPED. THPED is commercially available as NEUTROL TE from BASF.

The amount of the amine compound in the composition may be from about 0.1% to about 10% by weight of the composition, preferably from about 0.2% to about 5%, more preferably from about 0.25% to about 2.5%, and most preferably from about 0.5% to about 2%, by weight of the composition.

In certain embodiments of the invention, the weight ratio of Southernwood extract to amine compound in the composition is from about 0.3 to about 10, preferably from about 0.5 to about 5, more preferably from about 1 to about 4, and most preferably from about 2 to about 3.

Topical Compositions

The Southernwood extract may be combined with one or more cosmetically acceptable carriers to form a composition (e.g., formulation) suitable for use on visibly dry skin.

Suitable carriers of this invention include, but are not limited to, water, as well as diols or polyols, such as those having humectancy properties, including 1,2-propanediol, glycerin, propylene glycol, butylene glycol, polyethylene glycol (PEG), and combinations thereof. While in certain embodiments lower alcohols such as ethanol and isopropanol may be included, in other embodiments, in order to reduce likelihood of sky drying, these alcohols are excluded from the composition (e.g., present in less than 0.5%).

In order to facilitate treatment of visibly dry skin, in certain embodiments of the invention the cosmetically acceptable carrier includes both a humectant as well as an emollient. By emollient it is meant cosmetic ingredients that are generally insoluble in water and suitable for "leave on" applications for the skin.

The emollient may include a hydrophobic moiety that meets one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. One skilled in the art will recognize that emollients do not include amphiphilic molecules such as emulsifiers, surfactants and other surface active compounds. Amphilphilic molecules that will be understood to be excluded from emollients include those compounds that include both (a) a hydrophobic moiety defined above, and (b) a hydrophilic moiety, such as anionic, cationic, zwitterionic, or nonionic group, that is polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, hydroxyl, and poly(ethyleneoxy) sulfonyl. Emulsifiers, surfactants and other surface active compounds are commonly used for emulsification and wetting rather than for film-formation, spreading and the like.

Examples of emollients include mineral oils/waxes, including petrolatum; vegetable oils (glyceryl esters of fatty acids, triglycerides), waxes, other fatty esters. Specific non-limiting examples include, without limitation, isopropyl palmitate, isopropyl myristate, dimethicone, shea butter, petrolatum, C12-C15 alkyl benzoates, caprylic/capric triglycerides, various vegetable waxes, and mineral oil.

Various compounds may be included in the cosmetically-acceptable carrier to alter osmolarity and/or pH to acceptable levels. These include, but are not limited to sodium chloride, sodium phosphate monobasic, sodium phosphate dibasic, sodium hydroxide, and citric acid.

In order to facilitate the formulation of a suitable cosmetically-acceptable carrier, one may include any of various functional ingredients in the composition. For example, one may include any of a number of sequesterants, emulsifiers, thickeners, polymers, preservatives, colorants, fragrances, antioxidants, and other ingredients commonly used in personal care and cosmetic products. Suitable emulsifiers include, for example, non-ionic emulsifiers such as fatty alcohols including polyethoxylated fatty alcohols, esters of glycerol; anionic emulsifiers such as alkyl phosphates; cationic emulsifiers such as alkyl quaternary ammonium compounds. Suitable thickeners include hydrophobically modified acrylic polymers, cellulose polymers and clays.

While in certain embodiments (in which the product is in the form of a cleanser) cleansing surfactants such as betaines, sulfates, sulfonates, polyglycosides, among other wetting agents typically utilized for wetting and foam generation may be included, in other embodiments, in order to reduce likelihood of skin drying and to make the product suitable for a "leave-on" application, cleansing surfactants are excluded from the composition.

The pH chosen is not critical, but may be in a range, for example that is from about 4 to about 8, such as from about 5 to about 7.

The cosmetically acceptable carrier in the topical composition may constitute from about 40% to about 99.99%, by weight, of the composition, more preferably from about 80% to about 95%, by weight, of the composition. In a particularly preferred embodiment, the composition includes at least about 25% by weight water, more preferably at least about 50% by weight water. In other embodiments, the carrier (and the composition) is anhydrous. Such anhydrous compositions may be suitable for, for example, lip treatment products or color cosmetic (e.g., foundation).

In one embodiment, the compositions according to this invention may further contain one or more additional cosmetically active agent(s) as well as the above-mentioned components. What is meant by a "cosmetically active agent" is a compound, which may be a synthetic compound or a compound extracted, isolated, purified or concentrated from a natural source, or a natural extract containing a mixture of compounds, that has a cosmetic or therapeutic effect on the tissue, including, but not limited to: anti-microbial agents such as anti-yeast, anti-fungal, and anti-bacterial agents, anti-inflammatory agents, anti-aging agents, depigmentaion agents, anti-parasite agents, antioxidants, ant-acne agents, keratolytic agents, nutrients, vitamins, minerals, energy enhancers, sunscreens, sebum modulators, anti-cellulite agents and the like.

Examples of vitamins that may be constituents of the compositions of this invention include, but are not limited to, vitamin A, vitamin Bs such as vitamin B3, vitamin B5, vitamin B7 and vitamin B12, vitamin C, vitamin K, vitamin E such as alpha, gamma or delta-tocopherol, and their derivatives (such as salts and esters) and mixtures thereof.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention include, but are not limited to, extracts containing flavinoid, isoflavinoid, and their derivatives such as genistein and diadzein (e.g., such as soy and clover extracts, extracts containing resveratrol and the like. The one or more additional cosmetically active agent(s) may be present in any suitable concentration, such as, for example from about 0.01% to about 10% by weight.

Examples of anti-aging agents that which may be utilized in the compositions and methods of this invention include, but are not limited to, retinoids (e.g., retinol and retinyl palmitate).

Other examples of anti-aging actives include copper containing peptides; vitamins such as vitamin E, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, pyruvic acid; beta hydroxy acids such as beta-hydroxybutyric acid, beta-phenyl-lactic acid, beta-phenylpyruvic acid; polyphenolics; botanical extracts such as green tea, soy products, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable depigmentation agents include, but are not limited to soy products, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinoids, Kojic acid, soy products, and hydroquinone being particularly suitable examples.

Examples of sebum inhibitors include, for example, licorice root extracts, zinc salts such as zinc gluconate, dehydroacetic acid, and glycine derivatives. Examples of anticellulite agents include, for example, vasodilators such as green tea, and caffeine.

The Southernwood extract, amine compound and cosmetically acceptable topical carrier and optional additional cosmetically active agents may be combined in any proportion to form a composition suitable for topical use.

The composition may be formulated into any of various product types including, but not limited to solutions, suspensions, emulsions such as microemulsions and nanoemulsions, gels, solids and liposomes. The compositions may be made into a wide variety of cosmetic articles that include but are not limited to lotions, creams, gels, sticks, sprays, ointments, cleansing liquid washes and solid bars, pastes, foams, powders, mousses, wipes, strips, patches, wound dressings and adhesive bandages, hydrogels, film-forming products, as well as facial and skin masks. Other forms can be formulated by those of ordinary skill in the art.

The compositions may be topically applied to mammalian skin, preferably human skin. The skin may, in certain embodiments, be visibly dry or xerotic mammalian skin in order to reduce xerosis present on the face or body, including the hands, feet, scalp, elbows, knees, ankles, nape of the neck, among other areas portions of the skin.

In one embodiment, the compositions of the invention are used to treat mildly xerotic skin. In another embodiment, the compositions are used to treat moderately xerotic skin. In another embodiment, the compositions are used to treat skin having well-defined xerosis.

In certain other embodiments, topical compositions comprising Southernwood extract are topically applied to skin having compromised barrier properties, or skin characterized by certain disease states such as eczematic skin, psoriatic skin, or skin characterized by atopic dermatitis.

The compositions may be applied to the skin in need of such treatment according to a suitable treatment regimen, e.g., every month, every week, every other day, every day, twice a day, or the like.

According to the invention, the composition treats visibly dry skin by, inter alia, increasing the level of ceramides in such skin.

In certain embodiments of the invention, the compositions are applied to visibly dry skin in a manner sufficient to increase the expression of glucosyl ceramide synthase in such skin when tested according to the Gene Expression Test as described in Example 3 in this specification. In one embodiment, the composition is applied in a manner sufficient to increase the expression of glucosyl ceramide synthase after 5 days of treatment by at least 10%, preferably at least 15%, more preferably at least 20%, and most preferably at least 30%, as compared to the skin prior to such treatment.

In another embodiment, compositions of the invention are applied to skin having other need states, such as, for example, for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

In another embodiment, compositions of the invention are applied to skin in order to treat external aggressions in skin. Examples of external aggressions include, but are not limited to, damage to the skin from the use or cleansers (e.g., topical cleansers containing surfactants), make-up, shaving as well as environmental damage such as from UV light (e.g., sun-damage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

In another embodiment, compositions of the invention are applied to skin in order to treat skin in need of reducing skin inflammation. As used herein, "skin in need of reducing skin inflammation" means a skin exhibiting redness or erythema, edema. In certain other embodiments, "skin in need of reducing skin inflammation" refers to skin that is particularly reactive or sensitive to external elements. External elements include, but are not limited to, sun rays (UV, visible, IR), microorganisms, atmospheric pollutants such as ozone, exhaust pollutants, chlorine and chlorine generating compounds, cigarette smoke, cold temperature, heat. Inflammatory disorders and related conditions which may be treated or prevented by use of the compositions of this invention include, but are not limited to the following: arthritis, bronchitis, contact dermatitis, atophic dermatitis, psoriasis, seborrheic dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, postinflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, insect bites, folliculitis, alopecia, and secondary conditions and the like.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example I

Inventive Composition with Extract of Southernwood and THPED Shows Synergistic Moisturization Composition 1 according to the invention was made using the ingredients shown in Table 1.

TABLE 1

| INGREDIENT | CHEMICAL NAME | CONCENTRATION (wt. percent) |
|---|---|---|
| WATER PHASE | | |
| Deionized Water | Water | 83.00 |
| Ultrez 10 | Carbomer | 0.60 |
| Versene NA | Disodium EDTA | 0.20 |
| Emery 917 | Glycerin | 3.00 |
| OIL PHASE | | |
| Brij 72 | Steareth-2 | 0.50 |
| Brij 721 | Steareth-21 | 1.00 |
| Finsolv TN | C12-15 Alkyl Benzoate | 2.00 |
| Miglyol 812 | Caprylic/capric triglyceride | 2.50 |
| POST ADDITIONS | | |
| Dow Corning Q7-9120 Fluid 20 cst | Dimethicone | 2.00 |
| Phenonip XB | Phenoxyethanol (and) Methylparaben (and) Ethylparaben (and) Propylparaben | 1.00 |
| Neutrol TE | THPED | 1.00 |
| Sodium Hydroxide | Sodium Hydroxide | q.s. |
| Pulpactyl | aqueous-glycolic extract of Southernwood | 3.00 |
| Citric acid | Citric acid | 0.2 |

Composition 1 was prepared by adding water (Item#1) to a beaker, and the vessel was heated to 55-60 C. Versene and Ultrez 10 were added and the temperature was held at 55-60 C while it was mixed for 15 minutes or until homogeneous. In a separate vessel, the oil phase ingredients were mixed and held at 55-65 C. The oil phase was slowly added to the water phase. After the phases were completely mixed, the mixture was allowed to cool. When the temperature was below 50 C, dimethicone was added. Phenonip was added when the temperature was below 40 C. The mixture was allowed to mix for 10 minutes. Sodium hydroxide and/or citric acid was added to a target pH of 5.4. The mixture was allowed to mix for 10 minutes. PULPACTYL (Southernwood extract) and THPED were added, and the mixture was again allowed to mix for 10 minutes.

Comparative Composition A was prepared identically Composition 1, but without PULPACTYL. Additional water was included to compensate for the lack of PULPACTYL. Comparative Composition B was similarly prepared, except without THPED. Comparative Composition C (placebo) was also prepared the same way, except without PULPACTYL or THPED.

Composition 1 and Comparative Compositions A, B and C were tested for their ability to maintain skin hydration in the upper layers of the stratum corneum as follows.

A skin conductance meter, a SKICON200EX with MT-8C probe (available from I.B.S. Co. Ltd of Japan) that measures high frequency conductance in the upper layers of the stratum corneum level, was used as an indicator for degree of hydration.

Thirty human female subjects between the ages of 25 and 45 were evaluated for skin hydration on their legs, vertically from the ankle bone, using the SKICON device. Baseline measurements were performed prior to application of product.

A hand-held probe was placed on each of the two skin surface locations to take measurements. The probe sampled conductance at each surface location and measurements were taken in triplicate.

The subjects washed their legs with JOHNSON'S HEAD TO TOE BABY WASH daily for one week prior to the beginning of the study, as well as during the entire term of the study. Each subject applied either: Composition 1 to one leg and Comparative Composition A to the other leg, or Comparative Composition B to one leg and Comparative Composition C to the other leg. The test materials were applied two times per day for 4 weeks. After 3 weeks and after 4 weeks of treatment, SKICON measurements were again taken.

The difference between the high frequency conductance during one week of no product use following 4 weeks of product use (i.e., one week of regression) and the high frequency conductance at baseline was calculated for each subject. The percentage of subjects that showed a 10% or greater increase in high frequency conductance (cf. surface hydration) after one week of regression are shown in Table 2 below.

TABLE 2

| Test Composition | % of Subjects |
|---|---|
| Composition 1 (THPED + Extract of Southernwood) | 81.25* |
| Composition A (THPED) | 65.63 |
| Composition B (extract of Southernwood) | 55.17 |
| Composition C (neither extract of Southernwood, nor THPED) | 58.62 |

*$p < 0.05$ compared to Comparative Example, Comp. 2

The statistical analytical method employed was a t-test with a critical p value of 0.10. Composition 1 was also significantly better (t-test p=0.09) over Composition C.

The above results suggest the combination of both extract of Southernwood and THPED together provided surprisingly, significantly better skin surface hydration than the other test compositions after 4 weeks of treatment and 1 week of no product use. Applicants have previously shown that Southernwood extract improves skin barrier function and generates ceramides. However, the combination of Southernwood extract and an amine compound provides an additional, unexpected hydration benefit.

Example II

Inventive Composition with Extract of Southernwood and THPED Shows Enhanced Ability to Produce Ceramides, In-Vivo Composition 2 and Comparative Compositions D, E and F were prepared in a similar manner to the compositions of Example 1, except they included 0% rather than 3% glycerin, 5% rather than 2% dimethicone, 0.75% rather than 0.5% of steareth-2, and 1.5% rather than 1.0% of steareth-21.

Composition 2 was prepared according to the invention and contained 1% THPED and 2% PULPACTYL. Comparative Composition D contained 2% PULPACTYL, but no THPED. Comparative Composition E contained 5% PULPACTYL, but no THPED. Comparative Composition F (placebo) contained neither PULPACTYL nor THPED. As with Example 1 above, additional water was included to compensate for the lack of PULPACTYL or THPED as required.

Human female subjects between the ages of 25 and 45 were evaluated for ceramide production. The subjects washed their legs with JOHNSON'S HEAD TO TOE cleanser daily for one week prior to the beginning of the study, as well as during the entire term of the study. Each subject applied one test product per leg. The two test materials were applied two times per day for 3 weeks. Composition 2 and Comparative Compositions D and E were used by five subjects. Comparative Composition F was used by eight subjects. The test compositions were applied on the subject's legs, vertically from the ankle bone.

After 1 week and after 3 weeks of treatment, the treated skin of the subjects was subjected to a conventional tape stripping procedure to analyze for ceramide content. Tape strips were extracted for 1 hour at room temperature with 8 mL of a methanol:ethyl acetate mixture (80:20). After extraction, the tape strips was discarded and the solvent was evaporated to dryness under argon at room temperature. Thereafter, samples were stored at −20° C. until further analysis.

Each sample residue remaining after the tape strip condensation step was dissolved in 200 uL of a chloroform:methanol mixture (2:1). Twenty microliters and 40 uL of sample solution was applied on a high performance thin layer chromatography (HPTLC) plate (available from Whatman Partisil, GE Healthcare, Piscataway, N.J.) using an automatic sampler (CAMAG Automatic TLC Sampler 4, available from CAMAG Scientific Inc. of Wilmington, N.C.) and separated using the following sequential development system: (1) dichloromethane:ethyl acetate:acetone (80:16:4), (2) chloroform:methanol:acetone (76:16:8), (3) hexane:chloroform: acetic acid:acetone:methanol (6:80:0.1:10:4). The plates were stained with 3% copper acetate in 8% phosphoric acid and charred at 160° C.

Samples were applied in parallel for positional corrections and compared to a similarly prepared blank extract (tape strip without exposure to skin lipids). Quantification was performed against known quantities of Ceramide III standard (Cosmoferm) by densitometry. The calibration curve contained six concentrations of ceramide III: 1 ug, 2 ug, 4 ug, 8 ug, 12 ug, and 16 ug.

Each HPTLC plate was scanned (Hewlett-Packard Scanjet 8250 from Hewlett-Packard of Houston, Tex.) and quantified using image acquisition software (Image Pro 6.3 from MEDIA CYBERNETICS of Silver Spring, Md. The optical density of each ceramide band was measured and quantified against the standard calibration curve. Where both sample levels, 20 uL and 40 uL, were inside the linearity parameters of the calibration curve, an average of the two values was reported. All results outside the standard linearity parameters were disqualified. As one skilled in the art would appreciate, the resulting optical density will correlate with the amount of ceramide produced.

The results of the relative quantification of ceramide are shown in Table 3.

TABLE 3

| EXAMPLE | Optical Density (Absorbance Units or A. U.s) |
|---|---|
| Composition 2 (1% THPED + 2% Extract of Southernwood) | 113.9 |
| Composition D (2% extract of Southernwood) | 83.5 |
| Composition E (5% extract of Southernwood) | 113.3 |
| Composition F (neither extract of Southernwood nor THPED) | 64.3 |

While the application of a composition with 2% extract of Southernwood provided some improvement in ceramide production (83.5 A.U.s vs. 64.3 A.U.s or about 30%) over placebo, when 2% extract of Southernwood was used with 1% THPED, the amount of ceramides produced increased much more dramatically (77% over placebo). The amount of ceramides produced using the combination of Southernwood extract and THPED was comparable to or better than the level produced using a composition containing 2.5 times the amount of Southernwood extract (without THPED).

Example III

Inventive Composition

The following composition according to the invention was made.

TABLE 4

| INGREDIENT | CHEMICAL NAME | CONCENTRATION (wt. percent) |
|---|---|---|
| Brij 721 | Steareth-21 | 1.50 |
| Purified Water | Water | 67.75 |
| Cosvat | Chlorphenesin | 0.25 |
| Natrosol Plus 330 CS Modified Hydroxyethylcellulose | Cetyl Hydroxyethylcellulose; Sodium Phosphate; Disodium Phosphate; Silica; Hydrated Silica | 0.05 |
| Glycerin 99% USP | Glycerin | 8.00 |
| Varisoft TA 100 | Distearyldimonium Chloride | 5.00 |
| Propal NF | Isoproply Palmitate | 2.00 |
| Lanette 16 | Cetyl Alcohol | 1.25 |
| Dow Corning Q7-9120 Silicone Fluid 20 CST | Dimethicone | 2.50 |
| Benzyl Alcohol Pure NF | Benzyl Alcohol | 0.60 |
| Beantree Oil | Methylheptyl Isostearate | 2.00 |
| Ceraphyl ICA | Isocetyl Alcohol | 2.00 |
| Pulpactyl OP | Butylene Glycol; Artemisia Abrotanum Flwer/Leaf/Stem Extract | 2.00 |

TABLE 4-continued

| INGREDIENT | CHEMICAL NAME | CONCENTRATION (wt. percent) |
|---|---|---|
| NAB Mushroom PF | Algae Extract; *Ganoderma Lucidum* (Mushroom) Stem Extract; *Lentinus Edodes* Extract; Phenoxyethanol | 0.30 |
| Structure XL | Hydroxypropyl Starch Phosphate; Water | 2.00 |
| Isofol 28 Alcohol | Dodecylhexadecanol | 1.25 |
| Neutrol TE | Tetrahydroxypropyl Ethylenediamine | 1.00 |
| Waterfall Mod 307431 | Fragrance | 0.30 |
| Citric Acid Anhydrous | Citric Acid | 0.25 |

This composition was prepared by adding water to a process vessel, and heating the vessel 80-85 C. Natrusol Plus CS330 and glycerin were premixed and added to the batch. Elestab Ultra Pure CPN was added and the mixture was held for phasing. In a separate container, Varisoft TA 100, cetyl alcohol, beantree, ceraphyl ICA, isopropyl palmitate, dimethicone, Brij 721, and Isofol 28 were added together. They were mixed and heated to 80-85 C. When both phases were at 80-85 C, the oil phase was added to the water phase, and the resulting combination was mixed for 10 minutes at 80-85 C. The mixture was then removed from the heat and cooled to 40 C. In a separate container Neutrol TE and 1% water were mixed until dissolved. In another container, citric acid and water were mixed until dissolved, and then added to the Neutrol TE premix and mixed again until dissolved. At 45 C or below, the resulting Neutrol TE premix was added to the batch. At 40 C or below, NAB mushroom, Pulpactyl, and benzyl alcohol were added. The resulting mixture was mixed and cooled to 30-35 C. Water was added to QS minus the amount of Structure XL. The combination was mixed for at least 5 minutes, Structure XL was added and the resulting product was mixed until uniform.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

We claim:

1. A method of treating visibly dry skin, which comprises topically applying to said visibly dry skin a composition comprising an aqueous-glycolic Southernwood extract and an amine compound that is THPED,
   wherein the weight ratio of Southernwood extract to amine compound in said composition is about 2 to about 3.

2. The method of claim 1, wherein said visibly dry skin is xerotic skin.

3. The method of claim 1, wherein said skin is characterized by an eczematic disease state.

4. The method of claim 1, wherein said skin is characterized by a psoriatic disease state.

5. The method of claim 1, wherein said composition comprises from about 0.5% to about 10% of said Southernwood extract.

* * * * *